US00PP36884P2

(12) United States Plant Patent
van Swieten

(10) Patent No.: US PP36,884 P2
(45) Date of Patent: Aug. 12, 2025

(54) ***PHALAENOPSIS* PLANT NAMED 'PHA760527'**

(50) Latin Name: *Phalaenopsis hybrida*
Varietal Denomination: PHA760527

(71) Applicant: ANTHURA B.V., Bleiswijk (NL)

(72) Inventor: Martinus Nicolaas Gerardus van Swieten, Utrecht (NL)

(73) Assignee: ANTHURA B.V., Bleiswijk (NL)

( * ) Notice: Subject to any disclaimer, the term of this patent is extended or adjusted under 35 U.S.C. 154(b) by 0 days.

(21) Appl. No.: 19/017,727

(22) Filed: Jan. 12, 2025

Related U.S. Application Data

(60) Provisional application No. 63/679,023, filed on Aug. 2, 2024.

(51) Int. Cl.
*A01H 5/02* (2018.01)
*A01H 6/62* (2018.01)

(52) U.S. Cl.
USPC ..... Plt./311

(58) Field of Classification Search
USPC ..... Plt./311
See application file for complete search history.

*Primary Examiner* — Susan McCormick Ewoldt
(74) *Attorney, Agent, or Firm* — C. Anne Whealy

(57) ABSTRACT

A new and distinct cultivar of *Phalaenopsis* plant named 'PHA760527', characterized by its upright plant habit; relatively moderately vigorous to vigorous growth habit and moderate growth rate; strong flowering stems; healthy and sturdy leaves; freely flowering habit with typically three inflorescences developing per plant, each inflorescence with numerous flowers; pale yellow-colored flowers with darker yellow and red purple-colored labella; and good postproduction longevity.

2 Drawing Sheets

Figure 1:
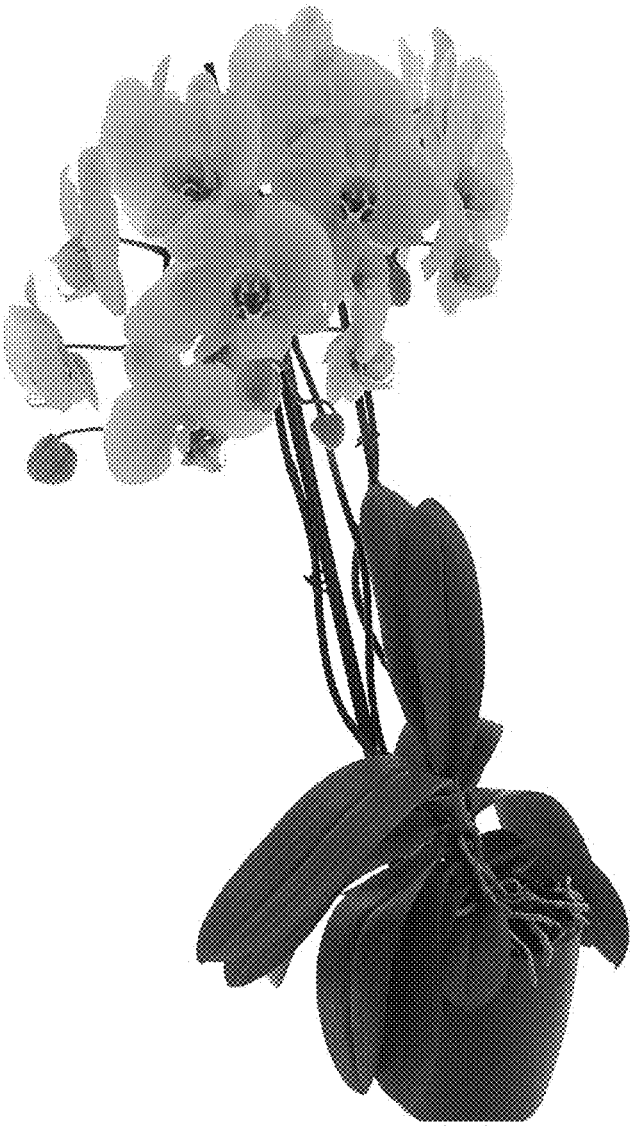

Botanical designation: *Phalaenopsis hybrida.*
Cultivar denomination: 'PHA760527'.

STATEMENT REGARDING PRIOR DISCLOSURES BY INVENTOR AND APPLICANT/ASSIGNEE

A European Community Plant Breeder's Rights application for the instant plant was filed by the Applicant/Assignee of the instant application, Anthura B.V. of Bleiswijk, The Netherlands on Aug. 17, 2023, application number 2023/1718, and published on Oct. 15, 2023. Foreign priority is not claimed to this application.

A U.S. Provisional Patent application for the instant plant was filed by the Inventor of the instant application, Mr. Martinus Nicolaas Gerardus van Swieten on Aug. 2, 2024. Domestic priority is hereby claimed to this U.S. Provisional Patent application Ser. No. 63/679,023.

BACKGROUND OF THE INVENTION

The present invention relates to a new and distinct cultivar of *Phalaenopsis* plant, botanically known as *Phalaenopsis hybrida*, commonly referred to as a *Phalaenopsis* or Moth Orchid and hereinafter referred to by the name 'PHA760527'.

The new *Phalaenopsis* plant is a product of a planned breeding program conducted by the Inventor in Bleiswijk, The Netherlands. The objective of the breeding program is to develop new medium-sized and freely flowering *Phalaenopsis* plants with flowers with unique and attractive patterns and coloration.

The new *Phalaenopsis* plant originated from a cross-pollination in August, 2017 in Bleiswijk, The Netherlands of a proprietary selection of *Phalaenopsis hybrida* identified as code number 13-056991-0002, not patented, as the female, or seed, parent with a proprietary selection of *Phalaenopsis hybrida* identified as code number 13-057810-0003, not patented, as the male, or pollen, parent. The new *Phalaenopsis* plant was discovered and selected by the Inventor as a single flowering plant from within the progeny of the stated cross-pollination grown in a controlled greenhouse environment in Bleiswijk, The Netherlands in May, 2020.

Asexual reproduction of the new *Phalaenopsis* plant by in vitro meristem propagation in a controlled environment in Bleiswijk, The Netherlands since May, 2020 has shown that the unique features of this new *Phalaenopsis* plant are stable and reproduced true to type in successive generations.

SUMMARY OF THE INVENTION

Plants of the new *Phalaenopsis* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'PHA760527'. These characteristics in combination distinguish 'PHA760527' as a new and distinct *Phalaenopsis* plant:

1. Upright plant habit.
2. Relatively moderately vigorous to vigorous growth habit and moderate growth rate.
3. Strong flowering stems.
4. Healthy and sturdy leaves.
5. Freely flowering habit with typically three inflorescences developing per plant, each inflorescence with numerous flowers.

6. Pale yellow-colored flowers with darker yellow and red purple-colored labella.
7. Good postproduction longevity.

Plants of the new *Phalaenopsis* can be compared to plants of the female parent selection. Plants of the new *Phalaenopsis* differ primarily from plants of the female parent selection in the following characteristics:

1. Leaf aspect of plants of the new *Phalaenopsis* is semi-erect to horizontal whereas leaf aspect of plants of the female parent selection is horizontal to semi-drooping.
2. Flower labella of plants of the new *Phalaenopsis* are not as broad as flower labella of plants of the female parent selection.
3. Cirrhose tips of plants of the new *Phalaenopsis* are longer than cirrhose tips of plants of the female parent selection.

Plants of the new *Phalaenopsis* can be compared to plants of the male parent selection. Plants of the new *Phalaenopsis* differ primarily from plants of the male parent selection in the following characteristics:

1. Flower petals of plants of the new *Phalaenopsis* pale yellow in color whereas flower petals of plants of the male parent selection are light yellow green in color.
2. The labella lateral lobes of plants of the new *Phalaenopsis* are more inwardly curved than the labella lateral lobes of plants of the male parent selection.
3. Cirrhose tips of plants of the new *Phalaenopsis* are yellowish green in color whereas cirrhose tips of plants of the male parent selection are reddish orange in color Plants of the new *Phalaenopsis* can be compared to plants of *Phalaenopsis hybrida* 'PHA402006', not patented. In side-by-side comparisons, plants of the new *Phalaenopsis* differ primarily from plants of 'PHA402006' in the following characteristics:

1. Flowers of plants of the new *Phalaenopsis* are not as broad as flowers of plants of 'PHA402006'.
2. The labella lateral lobes of plants of the new *Phalaenopsis* are more inwardly curved than the labella lateral lobes of plants of 'PHA402006'.

BRIEF DESCRIPTION OF THE PHOTOGRAPHS

The accompanying photographs illustrate the overall appearance of the new *Phalaenopsis* plant showing the colors as true as it is reasonably possible to obtain in colored reproductions of this type. Colors in the photographs may differ slightly from the color values cited in the detailed botanical description which accurately describe the colors of the new *Phalaenopsis* plant.

The photograph on the first sheet (FIG. 1) is a side perspective view of a typical flowering plant of 'PHA760527' grown in a container.

Figure 2:
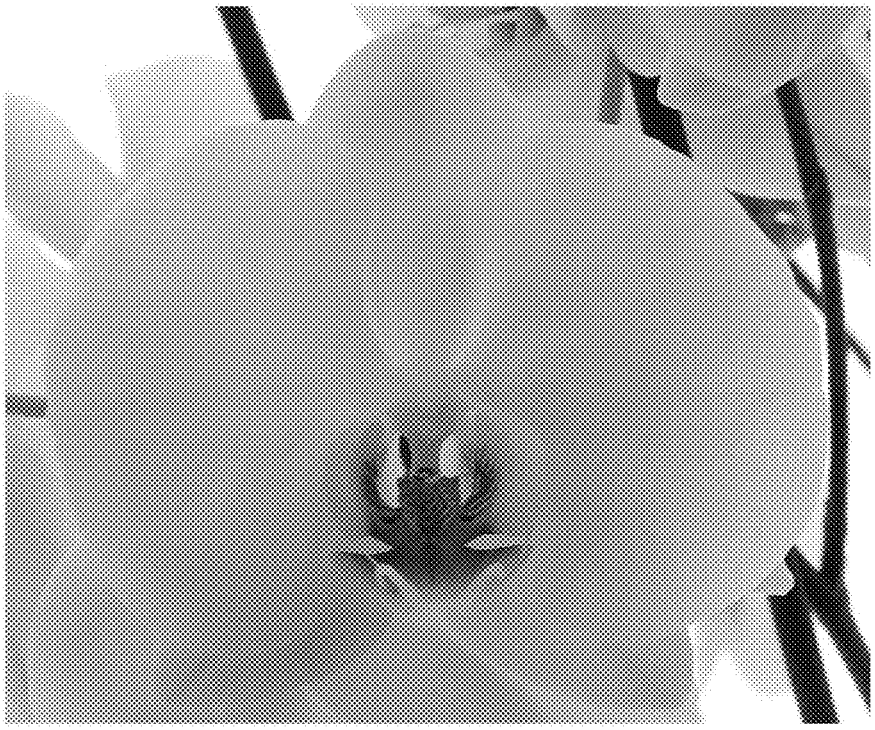

The photograph on the second sheet (FIG. 2) is a close-up view of a typical flower of 'PHA760527'.

DETAILED BOTANICAL DESCRIPTION

The aforementioned photographs and following observations and measurements describe plants grown during the early autumn in 12-cm containers in a glass-covered greenhouse in Bleiswijk, The Netherlands and grown under cultural practices typically used in commercial *Phalaenopsis* production. Plants were 18 months old when the photographs and description were taken. During the first 14 months of production of the plants, day and night temperatures averaged 28.5° C., and during the last four months of production of the plants, day and night temperatures averaged 20° C. Throughout the production of the plants, light levels ranged from 100 μmol to 180 μmol. In the following description, color references are made to The Royal Horticultural Society Colour Chart, 2015 Edition, except where general terms of ordinary dictionary significance are used.

Botanical classification: *Phalaenopsis hybrida* 'PHA760527'.

Parentage:

*Female, or seed, parent*.—Proprietary selection of *Phalaenopsis hybrida* identified as code number 13-056991-0002, not patented.

*Male, or pollen, parent*.—Proprietary selection of *Phalaenopsis hybrida* identified as code number 13-057810-0003, not patented.

Propagation:

*Type*.—By in vitro meristem propagation.

*Time to initiate roots, summer and winter*.—About two weeks at temperatures about 28° C. to 30° C.

*Time to produce a rooted young plant, summer and winter*.—About 20 to 25 weeks at temperatures about 28° C. to 30° C.

*Root description*.—Thick, fibrous; typically light green in color; actual color of the roots is dependent on substrate composition, water quality, fertilizer, substrate temperature and age of roots.

*Rooting habit*.—Freely branching; medium density.

Plant description:

*Plant form and growth habit*.—Herbaceous epiphyte; upright plant habit with typically three inflorescences developing per plant, each inflorescence with numerous flowers; monopodial; relatively moderately vigorous to vigorous growth habit and moderate growth rate.

*Plant height, substrate level to top of foliar plane*.—About 19.7 cm.

*Plant height, substrate level to top of floral plane*.—About 53 cm.

*Plant diameter or spread*.—About 34 cm.

Leaf description:

*Arrangement and quantity*.—Distichous, simple; sessile; about ten fully-developed leaves per plant.

*Length*.—About 18.6 cm.

*Width*.—About 6 cm.

*Aspect*.—Semi-erect to horizontal.

*Shape*.—Oblong to narrow obovate-oblong; very slightly carinate; moderately to strongly curled downward.

*Apex*.—Unequal obtuse with an abrupt acute tip.

*Base*.—Sheathing. Sheath length: About 1.8 cm. Sheath width: About 1.5 cm. Sheath color: Close to 144A and 144B slightly flushed with close to N186C.

*Margin*.—Entire; not undulate.

*Texture and luster, upper and lower surfaces*.—Smooth, glabrous; slightly to moderately glossy.

*Venation pattern*.—Camptodromous.

*Color*.—Developing leaves, upper surface: Close to NN137A and NN137B; narrow marginal edges, close to N199A. Developing leaves, lower surface: Close to 146A tinged with close to 200A and 200B; narrow marginal edges, close to N199A. Fully expanded leaves, upper surface: Close to 137B; narrow marginal edges, close to 152B; venation, close to NN137B. Fully expanded leaves, lower surface: Close to 146A and 146B very slightly tinged with close to 200A and 200B; narrow marginal edges, close to 152B and N199A; venation, close to 143A.

Inflorescence description:

*Appearance and flowering habit*.—Showy zygomorphic flowers arranged on axillary simple or branched racemes; typically three inflorescences develop per plant; each inflorescence with about twelve flowers; flowers face outwardly on outwardly arching inflorescences supported by upright peduncles; flowers with three petals, two lateral petals and one center petal transformed into a labellum and three sepals.

*Fragrance*.—None detected.

*Time to flower*.—Plants begin flowering about four months after planting; plants flower naturally during the winter into the spring.

*Flower longevity*.—Long flowering period, individual inflorescences maintain good substance for about eight weeks on the plant; flowers not persistent.

*Inflorescence length* (*lowermost flower to inflorescence apex*).—About 24.2 cm.

*Inflorescence width*.—About 16.9 cm.

*Flower buds*.—Height: About 1.7 cm. Diameter: About 1.3 cm by 1.7 cm. Shape: Broadly ovate. Color: Close to 150A and 150B slightly tinged with close to 153B.

*Flower size*.—About 8.1 cm (vertical) by 9.2 cm (horizontal).

*Flower depth*.—About 3.2 cm.

*Petals, quantity and arrangement*.—Three, two lateral petals and one center petal transformed into a labellum.

*Lateral petals*.—Length: About 4.2 cm. Width: About 6 cm. Shape: Broadly reniform to close to lunate. Apex: Obtuse. Margin: Entire; not undulate. Texture and luster, upper and lower surfaces: Smooth, glabrous, moderately velvety; matte. Color: When opening, upper surface: Distally, close to 154C and proximally, close to 154D. When opening, lower surface: Close to 154C and towards the base, close to 150C. Fully opened, upper and lower surfaces: Close to 2D; venation, close to 2D; color does not change with subsequent development.

*Labella*.—Appearance: Three-parted with two lateral lobes and a central lobe; overall shape, broadly cordate. Length, lateral lobes: About 2.3 cm. Width, lateral lobes: About 1.9 cm. Length, central lobe: About 2.2 cm. Width, central lobe: About 6 mm to 25 mm. Length, cirrhose tips: About 7 mm. Shape, lateral lobes: Obovate. Shape, central lobe: Deltoid with an elongated apex. Apex, lateral lobes: Obtuse. Apex, central lobe: Acute with two upwardly and backwardly curled cirrhose tips. Margins, lateral and central lobes: Entire. Texture and luster, lateral and central lobes, upper and lower surfaces: Smooth, glabrous, velvety; matte. Callosities: Located at the base of the labellum and attachment point of the lateral petals; about 5 mm in length, about 7 mm in width and about 6 mm in height. Color: When opening, upper surface: Lateral lobes: Close to 1A; towards the apex, close to 4B; at the base, blotch and stripes, close to 183C. Central lobe: Close to 154C and 175D; at the base, close to 145C with radial stripes, close to 183B; cirrhose tips, close to 154B. Callosities: Close to 22B; distally, close to 13B; densely covered with dots and blotches, close to 183B. When opening, lower surface: Lateral lobes: Close to 150C; towards the apex, close to 154D; towards the margins, close to 3A; at the base, slightly blotched, close to 176C. Central lobe: Close to 150C and 178B; at the base, close to 145B; cirrhose tips, close to 150B. Fully opened, upper surface: Lateral lobes: Close to 3B; towards the apex, close to 3C; towards the lower margin, close to 12A; at the base, blotch and stripes, close to 183C. Central lobe: Close to 1D and 173A; at the base, close to 150C with radial stripes, close to 183B; cirrhose tips, close to 2B. Callosities: Close to 22A; distally, close to 14B; densely covered with dots and blotches, close to 183B. Fully opened, lower surface: Lateral lobes: Close to 4B; towards the lower margin, close to 13B; at the base, blotched and striped with close to 183C. Central lobe: Close to 1D and 173A; at the apex, close to 6B; at the base, close to 150C with radial stripes, close to 183B; cirrhose tips, close to 2B.

*Sepals*.—Quantity and arrangement: Three, one upper dorsal sepal and two lower lateral sepals. Length, dorsal sepal: About 4.3 cm. Width, dorsal sepal: About 3 cm. Length, lateral sepals: About 4.3 cm. Width, lateral sepals: About 2.9 cm. Shape, dorsal sepal: Broadly oblong to broadly elliptic. Shape, lateral sepals: Ovate. Apex, dorsal sepal: Minutely retuse. Apex, lateral sepals: Bluntly acute. Base, dorsal and lateral sepals: Cuneate. Margins, dorsal and lateral sepals: Entire; not undulate. Texture and luster, dorsal and lateral sepals, upper and lower surfaces: Smooth, glabrous, moderately velvety; matte. Color, dorsal sepal: When opening, upper surface: Close to 2C; towards the apex, close to 2D. When opening, lower surface: Close to 154C; center, faintly tinged with close to 153D; towards the apex and margins, close to 154D. Fully opened, upper surface: Close to a blend of 1D and 2D; center, close to 3D; towards the base, close to a blend of 4D and 155A; venation, similar to lamina color. Fully opened, lower surface: Close to 1D; center, close to a blend of 3C and 3D; towards the base, close to 1D; venation, similar to lamina color. Color, lateral sepals: When opening, upper surface: Close to a blend of 1B and 1C; towards the base, close to 150C with dots, close to 175D. When opening, lower surface: Close to a blend of 150C and 151D. Fully opened, upper surface: Distally, close to a blend of 2D and 4D and proximally, close to a blend of 2C and 4C; at the base, dots, close to 176C and 176D; venation, similar to lamina color. Fully opened, lower surface: Close to 4C; towards the base, close to 4D and blotched at the base, close to 174D; venation, similar to lamina color.

*Peduncles*.—Length: About 56.5 cm. Diameter: About 5 mm. Strength: Strong. Aspect: Upright to outwardly arching. Texture and luster: Smooth, glabrous; matte. Color: Close to N200A densely covered with fine dots, and fine marbling, close to 147C and 147D.

*Pedicels*.—Length: About 4.2 cm. Diameter: About 3 mm. Strength: Moderately strong. Aspect: About 70° from peduncle axis. Texture and luster: Smooth, glabrous; matte. Color: Close to 152D; distal end, close to 144C; proximal end, close to 152B.

*Reproductive organs*.—Androecium: Column length: About 9 mm. Column width: About 6 mm. Column color: Close to 145D; towards the apex, close to 145C and 145D. Pollinia quantity: Two. Pollinia diameter (per two pollinia): About 2.75 mm. Pollinia color: Close to 23A. Gynoecium: Stigma length: About 3.5 mm. Stigma width: About 5 mm. Stigma shape: Reniform. Stigma color: Close to 145B. Ovary length: About 1 cm. Ovary diameter: About 1 mm. Ovary color: Close to 146D. Seeds and fruits: To date, seed and fruit development have not been observed on plants of the new *Phalaenopsis*.

Pathogen & pest resistance: To date, plants of the new *Phalaenopsis* have not been shown to be resistant to pathogens and pests common to *Phalaenopsis* plants.

Temperature tolerance: Plants of the new *Phalaenopsis* have been observed to tolerate high temperatures about 40° C. and are suitable for USDA Hardiness Zones 10 to 12.

It is claimed:

1. A new and distinct *Phalaenopsis* plant named 'PHA760527' as herein illustrated and described.

* * * * *